(12) United States Patent
Abdel-Monem et al.

(10) Patent No.: US 6,911,550 B2
(45) Date of Patent: Jun. 28, 2005

(54) DERIVATIVES OF SELENO-AMINO ACIDS WITH IMPROVED BIOAVAILABILITY AND METHOD FOR THEIR PREPARATION

(75) Inventors: Mahmoud M. Abdel-Monem, Moscow, ID (US); Michael D. Anderson, Eden Praire, MN (US)

(73) Assignee: Zinpro Corporation, Eden Prairie, MN (US)

( * ) Notice: Subject to any disclaimer, the term of this patent is extended or adjusted under 35 U.S.C. 154(b) by 0 days.

(21) Appl. No.: 10/372,491

(22) Filed: Feb. 21, 2003

(65) Prior Publication Data

US 2004/0254239 A1 Dec. 16, 2004

(51) Int. Cl.$^7$ .............................. C07F 3/06; A23K 1/00
(52) U.S. Cl. ........................ 556/134; 556/50; 556/63; 556/116; 556/148; 426/635
(58) Field of Search ............................ 556/50, 63, 116, 556/134, 148; 426/635

(56) References Cited

U.S. PATENT DOCUMENTS

| | | |
|---|---|---|
| 3,463,858 A | 8/1969 | Anderson |
| 3,925,433 A | 12/1975 | Abdel-Monem |
| 3,941,818 A | 3/1976 | Abdel-Monem |
| 3,950,372 A | 4/1976 | Abdel-Monem |
| 4,021,569 A | 5/1977 | Abdel-Monem |
| 4,067,994 A | 1/1978 | Anderson |
| 4,335,116 A | 6/1982 | Howard |

FOREIGN PATENT DOCUMENTS

| | | |
|---|---|---|
| CN | 1 252 273 A | 5/2000 |
| EP | 0 556 498 A2 | 8/1993 |

OTHER PUBLICATIONS

International Search Report from co-pending PCT/US03/39096.

Schrauzer, G. N., "Nutritional selenium supplements: product types, quality, and safety", Journal of the American College of Nutrition, 20(1) 2001, pp. 1–4, XP002281122.

Schrauzer, G. N., "Selenomethionine: a review of its nutritional significance, metabolism and toxicity", The Journal of Nutrition, 130(7) 2000, pp. 1653–1656, XP002281124.

Sugiura, Yukio et al., "Donor and ligand effects on acetylene reduction with cobalt (II)–thiol complex catalysts", Journal of the Chemical Society, Chemical Communications (1977), (21), 795–6, XP001189473.

Sugiura, Yukio et al., "Molybdothiol and molybdoseienol complex catalysts. Acetylene reduction and electron spin resonance characteristics", Advances in Chemistry Series (1980), 191 (Biomimetic Chem), 393–408, XP009031038.

Umehara, Hideki et al., "Preparation and some properties of cobalt (III) complex with D– and/or L–selenomethioninates", Bulletin of the Chemical Society of Japan (1987), 60(4), 1367–73, XP001189476.

Zainal, Hanaa A., et al., "Potentiometric and spectroscopic study of selenomethionine complexes with copper (II) and zinc(II) ions", Transition Metal Chemistry (London) (1995), 20(3), 225–7, XP009031035.

*Primary Examiner*—Porfirio Nazario-Gonzalez
(74) *Attorney, Agent, or Firm*—McKee, Voorhees & Sease, P.L.C.

(57) ABSTRACT

Metal L-seleno-alpha-amino acids salts and their use as a bioavailable feed and water ration supplement for domesticated animals such as cattle, pigs and poultry.

12 Claims, No Drawings

DERIVATIVES OF SELENO-AMINO ACIDS WITH IMPROVED BIOAVAILABILITY AND METHOD FOR THEIR PREPARATION

BACKGROUND OF THE INVENTION

The essential role of selenium in nutrition was first recognized by Schwarz and Foltz in 1957 (Schwarz, K. and Foltz, C. M., Selenium as an integral part of factor 3 against dietary necrotic liver degeneration. *J. Am. Chem. Soc.* 79:3292 (1957)). These researchers observed that rats developed liver necrosis when fed a purified diet deficient in vitamin E. However, the addition of selenium to the diet prevented the development of this condition. The ability of dietary selenium to prevent the development of exudative diathesis, a condition characterized by leakage of plasma into subcutaneous spaces of the abdomen and breast in chicken, was reported in the same year by Patterson et al (Patterson, E. L., Milstrey, R., Stokstad, E. L. R. Effect of selenium in preventing exudative diathesis in chicks. *Proc. Soc. Exp. Biol. Med.* 95: 617–620 (1957)). The important role of selenium in nutrition was further demonstrated by recognizing the practical effect of selenium deficiency in livestock (Muth, O. H., Oldfield, J. E., Remmert, L. F., and Schubert, J. R. Effects of selenium and vitamin E on white muscle disease. *Science* 128: 1090 (1958) and Hartley, W. J., and Grant, A. B. A review of selenium responsive diseases of New Zealand livestock. *Fed. Proc.* 2o: 679 (1961)). Subsequent work confirmed that selenium is an essential element for animals and that its deficiency results in various disorders (Combs, G. F. Jr., Combs, S. B. The role of selenium in nutrition. *Academic Press,* Orlando, Fla., pp 265–399 (1986b)).

The importance of selenium in human nutrition and the effects of its deficiency on human health were not recognized until the 1970s. Selenium deficiency was found to be one of the factors responsible for the Keshan disease, a human condition characterized by a dilated cardiomyopathy that affects persons living in rural areas of China. The incidence of the Keshan disease matched the distribution of selenium-deficient areas (Keshan Disease Research Group of the Chinese Academy of Medical Sciences. Epidemiologic studies on the etiologic relationship of selenium and Keshan disease. *Chin. Med J.* 92:477–482 (1979)). Furthermore, a prospective placebo-controlled study demonstrated that new cases of the disease can be prevented by the administration of sodium selenite tablets (Keshan Disease Research Group of the Chinese Academy of Medical Sciences. Observations on effect of sodium selenite in prevention of Keshan disease. *Chin. Med J.* 92:471–477 (1979)). The detrimental effects of diet-induced selenium deficiency in critically ill patients were reported in several case studies. Skeletal myopathy developed in one patient on total parenteral nutrition and was reversed by intravenous administration of selenomethionine (van Rij, A. M., Thomson, C. D., McKenzie, J. M., Robinson, M. F. Selenium deficiency in total parenteral nutrition. *Am. J. Clin. Nutr.* 32: 2076–2085 (1979)). Fatal cardiomyopathy induced by nutritional selenium deficiency was reported in a 43-year-old man receiving parenteral alimentation for 2 years before his death (Johnson, R. A., Baker, S. S., Fallon, J. T., Maynard, E. P., Ruskin, J. N., Wen, Z., Ge, K., and Cohen, H. J. An occidental case of cardiomyopathy and selenium deficiency. *The New England Journal of Medicine.* 304: 1210–1212 (1981)). In 1982, a second case of fatal cardiomyopathy associated with dietary selenium deficiency was reported in a patient on home parenteral nutrition for at least two years (Selenium Deficiency and Fatal Cardiomyopathy in a Patient on Home Parenteral Nutrition. *Gastroenterology.* 83:689–693 (1982)).

The recognition of the essential role of selenium in human and animal nutrition has resulted in the establishment of a Recommended Daily Allowance (RDA) for humans and approval of the inclusion of additional selenium compounds in animal feed. Recently, the Food and Nutrition Board of the Institute of Medicine revised the RDA for selenium to 55 $\mu$g (Dietary Reference Intakes for Vitamin C, Vitamin E, Selenium, and Carotenoids. Washington, D.C.: *National Academy Press,* (2000)). In 1974, the Food and Drug Administration (FDA) approved sodium selenite and sodium selenate as feed additive. These inorganic selenium salts can be added at the level of 0.3 ppm Se in feed dry matter. In June 2000, the FDA approved the use of selenium yeast in poultry broiler and layer diets.

The biochemical mechanism involved in manifesting the beneficial effects of selenium began to emerge in 1973 when selenium was found to be an essential component of the antioxidant enzyme glutathione peroxidase (Rotruck, J. T., Pope, A. L., Ganther, H. E., Swanson, A. B., Hafeman, D. G. F., and Hockstra, W. G. Selenium: Biochemical Role as a Component of Glutathione Peroxidase. *Science,* 179: 588–590 (1973) and Flohe, L., Gunzler, W. A. and Shock, H. H. Glutathione Peroxidase. A Selenoenzyme. *FEBS Lett.* 32: 132–134)). Concurrently, an extra cellular selenoprotein (Selenoprotein P) was discovered in rat, rhesus monkey and human plasma and found to be different than glutathione peroxidase. Selenoprtoein P is a monomeric glycoprotein that contains about 380 amino acid residues and up to 10 selenocysteine residue per the polypeptide chain. It is ubiquitous in mammalian tissues and accounts for more than 40% of the selenium concentration in human plasma. In human plasma in vitro, Selenoprotein P protects against peroxynitrite-mediated oxidation and reduces phospholipids hydroperoxide suggesting that it functions as an antioxidant in vivo. (Moschos M. P. Selenoprotein P. *Cellular and Molecular Life Sciences.* 57: 1836–1845 (2000)). Another function of selenium is as a catalytically active component of the iodothyronine deiodinase enzymes that regulates thyroid hormone metabolism. More recently, selenocysteine was identified in the active center of thioredoxin reductase demonstrating the role selenium plays in various metabolic processes catalyzed by these enzymes.

Recent studies have shown that the role of selenium in mammalians is not limited to the physiological functions of selenoenzymes. It now appears that selenium has a very specific role in spermatogenesis that is essential for male fertility. The selenoprotein phospholipids hydroperoxide glutathione peroxidase was found to play important roles during sperm maturation (Ursini F., Heim S., Kiess. M., Maiorino M., Roveri A., Wissing J., Flohe' L. Dual Function of the Selenoprotein PHGPx During Sperm Maturation. *Science* 285: 1393–1396 (1999)). The identification of a specific selenoenzyme in the sperm nuclei further underscored the important role selenium plays in sperm maturation (Pfeifer H., Conrad M., Roethein D., Kyriakopoulos A., Brielmeier M., Bornkamm G. W., Behne D. Identification of a Specific Sperm Nuclei Selenoenzyme Necessary for Protamine Thiol Cross-Linking During Sperm Maturation. *FASEB J* 15: 1236–1238 (2001)).

Selenium is present in selenoproteins in the form of selenocysteine. All mammalian selenoproteins identified so far are enzymes in which the selenocysteine residue is responsible for their catalytic function. Further studies of the complete amino acid sequence of mammalian glutathione peroxidase and the DNA analysis of its gene revealed that a specific codon is responsible for the insertion of selenocysteine into the amino acid chain of these enzymes. These results demonstrated that selenocysteine is the 21$^{st}$ encoded amino acid. This insertion is directed by a specific codon in mRNA. This codon is recognized by the anticodon of a specific tRNA which is first loaded with serine. The replacement of the side-chain oxygen of serine with selenium is catalyzed by a selenocysteine synthase to convert the seryl-tRNA into selenocysteyl-tRNA. Selenophosphate produced from selenide and ATP serves as the selenium donor in this reaction. Selenocysteine from selenocystyl-tRNA is incorporated into the selenoprotein at the ribosome.

Labeling rats and mice with $^{75}$Se indicated the presence of numerous selenium-containing proteins in mammalian tissues. Most importantly, a hierarchy in the distribution of selenium in the various tissues was discovered. This hierarchy ensures the preferential supply of selenium to certain proteins in certain organs and further illustrates the biological significance of selenium. When selenium intake is insufficient, the levels of selenium in some tissues such as the brain, the endocrine and the reproductive organs are maintained by preferential supply of dietary selenium and redistribution of the metabolized element. Extreme selenium depletion in rats resulted in a drastic decrease in selenium levels in most tissues to 1–3% control levels except for the brain which retained 60% of control level followed by spinal marrow, pituitary, thyroid, ovaries and adrenals (Behne D., Pfeifer H., Rothlein D., Kyriakopoulos A. Cellular and Subcellular Distribution of Selenium and Selenium-containing proteins in the rat. In: Roussel A. M., Favier A. E., Anderson R. A. (eds) *Trace Elements in Man and Animals* 10, Kluwer Academic/Pllenum Publishers New York, pp 29–34 (2000)). A further proof of the importance of selenium in mammalian is demonstrated by the finding that disrupting selenoprotein synthesis by knocking out the gene for selenocystyl-tRNA was lethal at the embryonic stage in mice. In contrast, severe selenium deficiency did not produce similar lethal effects probably due to the hierarchy in selenium distribution.

The dietary requirements for selenium are usually fulfilled by the ingestion of diets containing naturally occurring organic selenium compounds. Food and feed ingredients rich in organic selenium compounds include meat, fish, dairy products, some vegetables and grains. The concentration of selenium in materials of plant origin often depends on the concentration of selenium in the soil where the plants were grown. The soil of the Rocky Mountain States contains higher levels of selenium than other states and plants growing on these soils contain higher levels of selenium. The majority of organic selenium in natural food and feed ingredients is present as L-selenomethionine. Some accumulator plants and vegetables such as garlic, onions and broccoli growing on selenium rich soils contain Se-methylselenocysteine and its derivatives as the major organic selenium compounds. One of the predominant forms of selenium in native forage plants of the U.S. is selenate. Of 24 plants studied, selenate represented 5–92% of total selenium. Selenite was absent in all but one of these plants which contained 3% of total selenium as selenite. (Whanger P. D. Selenocompounds in Plants and Animals and their Biological Significance. *Journal of the American College of Nutrition*, 12: 223–232 (2002)). Regardless of the form in which the selenium is ingested, it is transformed by a variety of metabolic pathways via the same intermediary pool into the specific selenocysteine-containing selenoproteins which are responsible for selenium biological effects. The levels of these selenocysteine-containing selenoproteins in tissues appear to be homeostatically controlled. Ingestion of supplemental selenium above the optimal requirements does not appear to increase the concentrations of the specific selenoproteins in tissues. However, ingestion of selenomethionine results in higher retention of selenium in tissues than those observed with other sources of selenium. This is attributed to the fact that only a fraction of selenomethionine is metabolized similar to other sources of selenium via the intermediary pool to specific selenocysteine-containing proteins. A certain percentage of ingested selenomethionine is incorporated non-specifically directly into proteins in place of methionine. This non-specifically bound selenium is present in high concentrations in methionine rich proteins. The fraction of ingested selenomethione that is incorporated in non-specific proteins appears to be dependent on the ratio of selenomethionine to methionine and not selenium status. When low methionine diets are ingested, the increased non-specific incorporation of selenomethionine in proteins resulted in the decreased concentrations and effects of the specific selenoproteins. Non-specific incorporation of selenomethionine takes place in the proteins of skeletal muscles, erythrocytes, pancreas, liver, stomach, kidneys and the gastrointestinal mucosa. The release of selenomethionine from body proteins is linked to protein turnover. A steady state concentration of selenomethionine in tissues may be established if the intake of the seleno-amino acid is maintained over extended period of time. (Schrauzer G. N. Nutritional Selenium Supplements: Product Types, Quality, and Safety. *Journal of the American College of Nutrition*, 20: 1–4 (2001)).

The disposition of selenomethionine, Se-methylselenocysteine, selenite, and selenate in animals has been carefully studied. These common sources of selenium in animal nutrition take different pathways to the intermediary selenium pool which is ultimately incorporated in the specific seleno-proteins or further converted into polar metabolites that can be readily excreted. Below, these pathways are briefly described.

A fraction of ingested selenomethionine is converted to selenocysteine by the normal biochemical pathway involved in converting methionine to cysteine. Se-Adenosyl-selenomethionine is formed from selenomethionine and adenosine by a reaction catalyzed by S-Adenosylmethionine synthase. The conversion of Se-Adenosyl-selenomethionine to Se-adenosyl-selenohomocysteine is catalyzed by specific methyl transferases. The enzyme S-Adenosyl-homocysteine lyase converts Se-adenosyl-selenohomocysteine to seleno-homocysteine. The addition of selenohomocysteine to serine to form Se-cystathionine is catalyzed by cystathionine synthase, a PLP enzyme. Se-Cystathionine is converted to selenocysteine, ammonia and 2-ketobutyric acid in a reaction catalyzed by Cystathionine-γ-lyase. The enzyme Cysteine-β-lyase converts selenocysteine into hydrogen selenide, pyruvic acid and ammonia. Hydrogen selenide ($H_2Se$) is the key intermediary metabolite involved in the biosynthesis of specific seleno-proteins. The enzyme selenophosphate synthase catalyzes the reaction between hydrogen selenide and ATP to produce the reactive selenium compound selenophosphate ($H_3SePO_3$), AMP and orthophosphate. A specific enzyme, selenocysteine synthase then catalyzes the replacement of the side-chain oxygen of serine in a unique seryl-tRNA to give selenocysteyl-tRNA. Selenocysteine is transferred from selenocysteyl-tRNA and inserted in the forming selenoprotein chain on the ribosome.

Selenite is partially reduced to elemental selenium by dietary constituents such as ascorbic acid and by bacterial flora in the gastrointestinal tract. Absorbed selenite is readily reduced in two steps by four equivalents of glutathione to selenoglutathione trisulfide. The selenoglutathione trisulfide is reduced by glutathione in two steps to give hydrogen selenide and two moles of oxidized glutathione. hydrogen selenide serves as selenium source for the biosynthesis of selenoproteins as described above. If selenate is ingested as the selenium source, it is first reduced by two equivalents of glutathionine to selenite which is then converted to hydrogen selenide.

A fraction of the ingested selenium source is eliminated via a number of pathways. Some of orally ingested selenite and selenate is reduced in the gastrointestinal tract to elemental selenium which is excreted in feces. Selenite and selenate are also excreted in urine. Enzymatic methylation of hydrogen selenide gives the volatile metabolite methyl selenol which can be excreted by the lungs. Methyl selenol is further methylated in a stepwise fashion first to the volatile metabolite dimethyl selenide which is excreted by the lungs and then to the polar trimethylselenonium cation which is eliminated in the urine.

Supplementation of animal feed with an approved source of selenium is gaining popularity. Currently, inorganic sources such as selenite and selenate as well as the organic source selenium yeast are approved by the FDA as feed ingredients. However, the amount of selenium that can be added and the species of livestock that may be supplemented are regulated. The approval of the use of the inorganic sources of selenium such as selenite and selenate as feed ingredients is curious since these do not occur naturally in significant concentrations in feed. L-Selenomethionine is the form of selenium most commonly present in natural foods and feed. However, synthetic L-selenomethionine has not been commercially available at reasonable prices for use as feed ingredient in livestock production. Therefore, selenium enriched yeast has been used as a practical affordable source of L-selenomethionine. Special strains of *Saccharomyces cerevisiea* grown in a selenium rich medium accumulate as much as 3000 $\mu$g Se per g dry matter. Most of the selenium in yeast exists as L-selenomethionine. The L-selenomethionine is present primarily incorporated in the yeast protein in place of L-methionine. Other organic selenium compounds may be present in low concentrations including Se-adenosyl-selenohomocysteine (2–5%), selencysteine (0.5%), methylselenocysteine (0.5%), selenocystathionine (0.5%), and $\gamma$-glutamyl-Se-methylselenocysteine (0.5%). Only traces of inorganic selenium may be present in the yeast as selenite or selenate (Schrauzer G. N. Selenomethionine: A Review of its Nutritional Significance, Metabolism and Toxicity. *J. Nutr.* 130: 1653–1656 (2000)).

Several studies were published during the last several years comparing the effects of selenite and selenium yeast supplements on the selenium status and health of livestock. Especially in selenium deficient animals, the selenium concentrations in plasma and tissues increase linearly as intake of selenium increases to a point after which plasma and tissue selenium concentrations do not change significantly with increased intake. For example the relationship of dietary selenium from sodium selenite to selenium concentrations in plasma and milk in dairy cows was examined by Maus et al. Selenium concentration in plasma and milk increased linearly as intake of selenium increased from about 2–6 mg/day. Further increases in intake resulted in only little change in plasma and milk selenium (Maus R. W., Martz F. A., Belyea R. L. and Weiss M. F., Relationship of Dietary Selenium to Selenium in Plasma and Milk from Dairy Cows, *J Dairy Sci*, 63: 532–537-(1980)).

Selenium was found to be more bioavailable from selenium yeast than from selenite or selenate in several animal studies. The increase in tissue selenium concentration was greater in animals fed selenium yeast compared to animals fed selenite. However, the increase in glutathione peroxidase activity was about the same regardless of the source of supplemental selenium. The favorable effects of selenium supplementation on animal health were demonstrated in several studies. For example, selenium supplementation improved udder health in dairy cows as demonstrated by a decrease in the percent quarters harboring mastitis pathogens and a decrease in somatic cells count in milk. Again the effects of selenium yeast were greater than those of sodium selenite (Malbe M., Klassen M., Fang W., Mylls V., Vikerpuur M., Nyholm K., Sankari S., Sourta K., and Sandholm M. Comparisons of Selenite and Selenium Yeast Feed Supplements on Se-incorporation, Mastitis and Leucocyte Function in Se-deficient Dairy Cows, *J Vet Med A*, 42: 111–121 (1995)).

It is now well established that dietary selenium is essential for the health and wellbeing of humans and animals. Several studies have demonstrated that selenium is more bioavailable from organic sources than from inorganic sources. The only organic selenium source available for commercial use is selenium rich yeast preparation. In yeast, selenium exists primarily as L-selenomethionine rich proteins. Although Selenium yeast is now widely accepted as a source of dietary selenium, its use suffers from several shortcomings. The concentration of organically bound selenium in yeast is limited by its ability to form L-selenomethionine from the selenite enriched media. Currently, the highest possible concentration of selenium in yeast appears to be 2000 $\mu$g/g dry matter. Secondly, since the organically bound selenium in yeast is produced by a biological process that is vulnerable to subtle variations in the large scale production process, the exact composition of the selenium compounds is variable and is not readily known. Occasionally, yeast contains variable concentrations of inorganic selenium compounds such as selenites and selenates. Thirdly, the organic selenium compounds are present in yeast as part of the intracellular proteins. Before these compounds are available for absorption after being ingested, the cell walls of yeast must rupture to release the protein into the animals' gastrointestinal tract where it can be subjected to the proteolytic effects of digestive enzymes. It is only after the protein is hydrolyzed to single amino acids or dipeptides that the selenium compounds can be absorbed. The release of the selenium compounds as single amino acids or dipeptides from the intact yeast cells is not complete and is highly dependent on the conditions in the gastrointestinal tract. Because of these shortcomings, it is important to develop alternatives to selenium enriched yeast to serve as a readily bioavailable dietary source of selenium.

Recently, synthetic seleno-amino acids became commercially available at a reasonable cost. These amino acids have low water solubility and their crystals have water repellent properties that result in low rate of dissolution. Low solubility and slow rate of dissolution lower the bioavailability of these compounds after feeding to animals.

Recently, the demand for a dietary sources of selenium with improved bioavailability for use as a supplement for human and livestock. has increased. Synthetic seleno-amino acids have recently become commercially available at a reasonable cost. These amino acids have low water solubility and their crystals have water repellent properties that result in low rate of dissolution. Low solubility and slow rate of dissolution lower the bioavailability of these compounds after feeding to animals. One objective of this invention is to identify derivatives of seleno-amino acids with improved bioavailability.

The inventors of this patent application have in the past disclosed 1:1 complexes of essential metals and amino acids as means of improving the bioavailability of these metals after ingestion in livestock, see for example U.S. Pat. Nos. 3,941,818, 3,925,433, 3,950,372, 4,021,569, and 4,067,994. The purpose of forming these complexes is to increase the solubility of the metal and increase its stability in chemical environment of the gastrointestinal tract of the animal. Although the increased bioavailability of the trace metal was anticipated and consistently demonstrated in numerous studies, the increased bioavailability of the amino acid ligand was not anticipated. Because of its unique chemical properties, selenium in contrast to the essential metals previously described in our patents does not form complexes with amino acids. Therefore, it was necessary to find a different strategy to improve the bioavailability of selenium.

Selenium like sulfur, is a member of group VIA elements. It exists in different allotropic forms and has oxidation states of −2, 0, +2, +4, and +6. Selenium is a nonmetallic element. It can form mono-atomic anions and therefore can form ionic as well as covalent bonds. In the oxidation state −2, selenium forms covalent bonds with carbon substituents and can often replace sulfur in naturally occurring compounds. The biological role of selenium is attributed to these naturally occurring compounds in which selenium exists in the −2 oxidation state and is covalently bound, usually with carbon as part of functional proteins. Seleno-amino acids have been proposed as dietary sources of selenium. However, it is recognized that the bioavailability of these compounds may be significantly diminished by the nutritional status of the animal and the composition of the diet and gastrointestinal tract contents. Therefore it was desirable to explore reversible derivatives of the seleno-amino acids that may improve the bioavailability of these amino acids. The improved bioavailability of essential metals from the 1:1 amino acid complexes did not provide any knowledge on the relative bioavailability of the amino acid ligands. Indeed, the common knowledge that amino acid are absorbed from the gastrointestinal tract by a highly specialized mechanisms indicated that the formation of these complexes will not have a significant effect on the bioavailability of the amino acid. Therefore it was surprising that these complexes demonstrated improved bioavailability of the seleno-amino acid when used as a ligand.

The primary object of the present invention is to make novel 1:1 metal complexes of seleno-amino acids with improved bioavailability.

Another object of the invention is to describe methods of preparation of these derivatives and their use as feed ingredients in livestock.

SUMMARY OF THE INVENTION

The primary objective of this invention is the development of new compounds that are intended to enhance the bioavailability and/or increase the stability of seleno-amino acids. The 1:1 metal complexes of the seleno-amino acids were found to be very readily soluble in water and their solutions are stable on storage. Because of water solubility, a solution of the complex can be blended with other feed ingredients easier than the amino acid itself. These complexes are more bioavailable than the amino acids in feeding studies in a number of species of livestock. The complex appears to be resistant to rumen degradation after ingestion in rumen which increases their usefulness as dietary sources of selenium in ruminants such as cows and sheep. A manufacturing process was developed in which the reaction between the seleno-amino acid and the metal salt and the formation of a concentrated premix of the metal seleno-acid amino complex was accomplished in the final shipping container which resulted in minimum handling of the seleno-amino acid, making the process safe and economical.

DETAILED DESCRIPTION OF A PREFERRED EMBODIMENT

Because of unsatisfactory performance of presently available selenium sources for use in feed supplements, it was necessary then to explore derivatives of selenomethionine that are readily soluble in water and has improved bioavailability. The metal L-selenomethionine 1:1 complexes were found to meet these criteria as well as possess additional useful properties. For example, the zinc L-selenomethionine complex (Formula 1) is very readily soluble in water and its solution is stable on storage. Because of its water solubility, a solution of the complex can be blended with other feed ingredients easier than the amino acid itself. This complex was more bioavailable than the amino acid in feeding studies in a number of species of livestock. Of special interest is that the complex appears to be resistant to rumen degradation after ingestion in rumen which increases its usefulness as a dietary source of selenium in ruminants such as cows and sheep.

Other commercially available seleno-amino acids were found to posses similar undesirable physical properties as L-selenomethionine. Formation of the metal complexes of these seleno-amino acids improved their physical properties in a fashion similar to that of L-selenomethionine. For example, zinc Se-methyl-L-selenocysteine complex is readily soluble in water to give a stable solution. This complex is more bioavailable than the parent seleno-amino acid.

FORMULA 1:
Molecular structure of zinc L-selenomethionine complex.

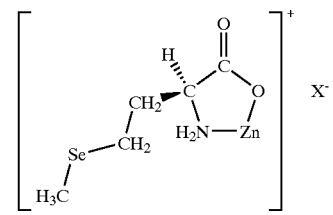

X⁻ = Chloride, hydrogen sulfate

As can be seen from the structural formula of the zinc L-selenomethionine complex (Formula 1), the compounds described in this invention exist as Ion pairs in which the cation is the seleno-amino acid metal complex. The selection of the anion is not critical. The anion can be either inorganic or organic anion. A monovalent, a divalent or a polyvalent anion may be used as long as it is recognized that the number of the monovalent metal seleno-amino acid complex cations will equal the valency of the anion cation in the neutral ion pair. Preferably, an inorganic acid such as halogen acids, sulfuric acid or phosphoric acid is used as the source of the anion. Most preferably, chloride or hydrogen sulfate is used as the anion. Organic anions may include monobasic aliphatic acids (e.g. acetic, propionic acids), dibasic aliphatic acids (e.g. succinic and adipic acids), substituted aliphatic acids (e.g. chloroacetic acid), aromatic acids (e.g. benzoic acid), or aralkyl acids (e.g. phenylacetic acid).

The amino acid used is preferably methionine but others can also be used to form the 1:1 selino-2 amino acid complex. For example, in formula 1 above, the methionine moiety can be replaced with arginine, histidine, isoleucine, leucine, lysine, phenylalanine, threonine, tryptophan and valine.

A number of metal ions can be used to form the 1:1 complexes with the seleno-amino acids such as zinc, manganese, copper, cobalt, iron and chromium. The preferred metals are zinc, cobalt and manganese. If oxidizing metals such as copper and iron are used, special care must be taken to avoid the slow oxidation of the seleno-amino acid that will result in decomposition of the complex. The preferred metal ion for the formation of the cationic 1:1 complex is zinc because of the stability of its complexes and its low oxidation potential. Additionally, zinc salts such as zinc chloride and zinc sulfate of high purity are readily commercially available at a reasonable cost.

Because of the toxicity of selenium compounds, and the high cost of L-selenomethionine it was important to develop a process for manufacturing these metal L-selenomethionine complexes that is safe and economical. A manufacturing process was developed in which the reaction between L-selenomethionine and the metal salt and the formation of a concentrated premix of the metal L-selenomethionine complex was accomplished in the final shipping container. This resulted in minimum handling which made the process safe and economical. In this process a suitable mixer was devoted for the manufacturing of a premix containing as much as 5% selenium as zinc L-selenomethionine chloride. Appropriate mixer paddles were machined to fit the final shipping containers for the product. The final shipping container was used as the mixing bowl and a shroud was attached around the mixer paddle that fit tightly over the mixing bowl and prevented the loss of any of the mixing bowl contents during mixing. A solution of the metal salt, usually zinc chloride was heated to 80–95° C., preferably 85–90° C. The hot solution is placed into the mixing bowl, the required amount of the L-selenomethionine is added and the cover shroud is fitted over the container. The zinc chloride and L-selenomethionine were used in equimolar concentrations. The contents were mixed thoroughly until the L-selenomethionine was completely dissolved and the zinc L-selenomethionine chloride is formed. A high adsorbing carrier such as silica is then added, the container covered and the contents mixed thoroughly until a homogeneous product is obtained. The use of a carrier with water adsorbing properties avoids the requirement for drying the product. This minimizes handling of the toxic selenium compounds. Any suitable carrier may be used as long as it has a high water adsorbing capacity. The preferred carrier is powdered silica. The mixing times must be adjusted to ensure that the active ingredient zinc L-selenomethionine is evenly distributed throughout the carrier.

The preferred additive levels to solid or liquid feed or water rations will depend on the animal being supplemented. but will generally be an amount within the range of 0.01 ppm to 2.00 ppm, preferably 0.05 ppm to 0.5 ppm. For swine and poultry, the diet will be supplemented by 0.05–2.00 ppm Se, preferably 0.1–0.3 ppm Se. For cattle, the feed will be supplemented by 0.05–10 mg Se per head per day, preferably 2–7 mg Se per head per day.

The following examples are offered to illustrate the practical methods of obtaining these complexes, their properties, and their use as sources of selenium in animal nutrition.

EXAMPLE 1

Preparation and Properties of Zinc L-Selenomethionine Hydrochloride:

L-Selenomethionine (97.8 mg, 0.5 mmole) was added to water (45 ml) in a 250-ml round bottom flask placed in an ice-bath. The mixture was vigorously stirred by using a magnetic stirrer and a Teflon coated stir-bar. The powder did not completely go into solution and floated on the surface of the water as soon as stirring was stopped. Zinc chloride (68.20 mg, 0.5 mmole) was added with continued stirring. A clear solution was immediately formed. The solution was concentrated to dryness at temperature 40° C. under reduced pressure. A hygroscopic colorless solid was formed. The solid was readily soluble in water.

The FTIR spectrum of the solid in a potassium bromide pellet showed absorption peaks at about: 3510.2(vs), 3143.8 (s), 2927.7(m), 1639.4(vs), 1488.9(m), 1411.8(m), 1338.5 (m), 1218.9(w), 1130.2(w), 578.6(w), and 536.2(w) cm$^{-1}$. (w, weak; m, medium; s, strong; vs, very strong). This spectrum is different than that of L-selenomethionine which showed absorption peaks at about: 3433.1(w), 2923.9(s), 2731.0(m), 2611.4(m), 2117.7(w), 1608.5(s), 1581.5(vs), 1512.1(s), 1411.8(s), 1338.5(m), 1269.1(w), 1218.9(w), 1153.4(w), and 540.0(w) cm$^{-1}$.

A solution containing 1 mg/ml of zinc L-selenomethionine hydrochloride in water was analyzed by HPLC using three different column/mobile phase systems. In all systems, a UV/Vis detector at 210 nm was used and 20 μl of the sample was injected onto the column by using a Rheodyne Loop injector. In the first system a 100×4.6 mm, Adsorbosphere HS $C_{18}$ OPA 5μ column (Alltech Associates, Inc.) was used. The mobile phase was 0.9% sodium chloride in water at a rate of 1 ml/min. In this system, the retention times for L-selenomethionine and zinc L-selenomethionine were 2.406 and 2.347 min, respectively. This very small difference in retention times between the seleno-amino acid and its zinc complex was consistent. However, changing the chromatographic conditions did not improve the separation. In the second system a 250×4.6 mm, Transition Metal 7μ column (Alltech Associates, Inc.) was used with a 5 mM sodium acetate pH 5.8 buffer at a rate of 1 ml/min as mobile phase. In this system the zinc L-selenomethionine hydrochloride had a retention time of 6.675 min. In the third system a 250×4.6 mm Discovery Cyano column (Supelco) was used with 0.1% Acetic Acid at 1 ml/min as the mobile phase. Zinc L-selenomethionine had a retention time of 4.167 min. In the last two systems it was not possible to see a difference in retention times between L-selenomethionine and zinc L-selenomethionine. In all these system a single peak accounting for over 99% of detector response was obtained. All three systems were useful for the determination of zinc L-selenomethionine in premixes.

EXAMPLE 2

Preparation of Zinc L-Selenomethionine 5% Selenium Premix:

Zinc Chloride (166.898 g, 1.2 moles) was mixed with boiling water (500 ml) in a stainless steel mixer bowl. L-Selenomethionine (196.110 g, 1.0 moles) was added to the zinc chloride solution. The mixture was mixed until a homogenous solution was formed. A 600 g of silica powder (Tixosil, Rhodia, Brazil) was added slowly with continued mixing until a homogenous powder was obtained. The powder is transferred into a suitable container, covered tightly, and/stored in a cool dry place. This concentrated premix contained 5% selenium and can be diluted by blending with a suitable carrier such as calcium hydrogen phosphate to the desired concentration of selenium in the final premix.

A 2.0 g sample of the concentrated premix (5% Se) was accurately weighed and extracted with water. The extract was transferred into 100-ml volumetric flask and completed to volume with water. The extract was analyzed as follows: FTIR Identification: A 100 µL of the extract was added to 100 mg of FTIR grade potassium bromide powder and mixed well. The mixer was dried in an oven at 75° C. A pellet was formed and the FTIR spectrum of the sample was recorded. The FTIR spectrum showed absorption peaks at about: 3510.2(vs), 3143.8(s), 2927.7(m), 1639.4(vs), 1488.9 (m), 1411.8(m), 1338.5(m), 1218.9(w), 1130.2(w), 578.6 (w), and 536.2(w) $cm^{-1}$. (w, weak; m, medium; s, strong; vs, very strong). This spectrum is different than that of L-selenomethionine. Of interest is the absence of the weak to medium band at around 2118 $cm^{-1}$ characteristic of free amino acids.

HPLC Determination: The concentration of zinc L-selenomethionine in the water extract was determined by HPLC. A Shimadzu instrument composed of SCL-10A-VP Controller, Dual LC-10AD-VP Pumps, SIL-10 Ai Auto sampler, and SCD-10AV-VP UV/Visible Detector set at 210 nm. A Discovery Cyano 5µ column (25 cm×4.6 mm) was used at 25° C. The mobile phase was a 0.1% Glacial acetic Acid at 1.00 mL/min. A 50 µL of the standard or sample solution was injected by the auto sampler. A set of 5 standards were prepared to contain 0.1567, 0.3134, 0.4701, 0.6268, and 0.7835 mg/ml of Zinc L-Selenomethionine. A 100 µL of the sample extract was diluted with 900 µL water and used as sample solution. Standards and sample solutions are filtered through a 2µ filter before injection. Standards and sample contained only a single component with a retention time of 3.975 min. Linear regression was used to construct a correlation graph of area under the peak vs. concentration. The concentration of zinc L-selenomethionine in the sample solution was calculated from the correlation graph and found to be 0.3898 mg/mL corresponding to 18.79% Zinc L-Selenomethionine or 5.67% Selenium in the original Premix.

EXAMPLE 3

Stability of a Zinc L-Selenomethionine Solution:

About 2.0 g of a Zinc L-Selenomethionine Premix 5% Se was accurately weighed and transferred into a 100-ml volumetric flask. Water was added to volume. The flask was stoppered and its contents were mixed vigorously. The mixture was allowed to settle and a sample of the supernatant was removed carefully and filtered through a 2 µL filter. The concentration of zinc L-selenomethionine in the filtrate was determined by HPLC as described in EXAMPLE 2. Analysis was conducted immediately after the solution was prepared and repeated at 30 days and 90 days after storing at an ambient temperature averaging 18° C. and 50% relative humidity. The concentrations of zinc L-selenomethionine in the solution was found to be 18.95, 18.89, and 18.78% on the day of preparation, after 30 and 90 days, respectively. These results indicate that the concentration of the zinc L-selenomethionine in the solution changed by less than 0.5% over a thirty day storage at ambient temperature and humidity.

EXAMPLE 4

Preparation of Zinc L-Se-Methylselenocysteine Hydrochloride:

Zinc Chloride (8.447 g, 0.05 moles) was mixed with boiling water (25 ml) in a stainless steel mixer bowl. Se-Methyl-L-selenocysteine (9.1873 g, 0.05 moles) was added to the zinc chloride solution. The mixture was mixed until a homogenous solution was formed. A 30 g of silica powder (Tixosil, Rhodia, Brazil) was added slowly with continued mixing until a homogenous powder was obtained. The powder is transferred into a suitable container, covered tightly, and stored in a cool dry place. This concentrated premix contained 5% selenium and can be diluted by blending with a suitable carrier such as calcium hydrogen phosphate to the desired concentration of selenium in the final premix.

A 2.0 g sample of the concentrated premix (5% Se) was accurately weighed and extracted with water. The extract was transferred into 100-ml volumetric flak and completed to volume with water. The extract was analyzed as follows: FTIR Identification: A 100 µL of the extract was added to 100 mg of FTIR grade potassium bromide powder and mixed well. The mixer was dried in an oven at 75° C. A pellet was formed and the FTIR spectrum of the sample was recorded. The FTIR spectrum showed absorption peaks at about: 3529.5(vs), 3159.2(s), 2927.7(m), 1639.4(vs), 1477.4 (m), 1419.5(m), 1396.4(m), 1342.4(m), 1296.1(w), 1122.5 (w), 578.6(w), and 536.2(w) $cm^{-1}$. (w, weak; m, medium; s, strong; vs, very strong). This spectrum is different than that of L-Se-Methylselenocysteine. Of interest is the absence of the weak to medium band at around 2118 $cm^{-1}$ characteristic of free amino acids.

HPLC Determination: The concentration of zinc L-Se-Methyselenocysteine in the water extract was determined by HPLC. A Shimadzu instrument composed of SCL-10A-VP Controller, Dual LC-10AD-VP Pumps, SIL-10 Ai Auto sampler, and SCD-10AV-VP UV/Visible Detector set at 210 nm. A Discovery Cyano 5µ column (25 cm×4.6 mm) was used at 25° C. The mobile phase was a 0.1% Glacial acetic Acid at 1.00 mL/min. A 50 µL of the standard or sample solution was injected by the auto sampler. A set of 5 standards were prepared to contain 0.14942, 0.29884, 0.44826, 0.59769, and 0.74711 mg/ml of Zinc L-Se-Methylselenocysteine. A 100 µL of the sample extract was diluted with 900 µL water and used as sample solution. Standards and sample solutions are filtered through a 2µ filter before injection. Standards and sample contained only a single component with a retention time of 3.842 min. Linear regression was used to construct a correlation graph of area under the peak vs. concentration. The concentration of zinc L-Se-Methylselenocystein in the sample solution was calculated from the correlation graph and found to be 0.3944 mg/mL corresponding to 17.25% Zinc L-Se-methylselenocysteine or 5.50% Selenium in the original Premix.

EXAMPLE 5

Comparison of the Effects of Sodium Selenite and Zinc L-Selenomethionine on Glutathione Peroxidase and Tissue Selenium Concentrations in Lambs:

Twenty-four (32) lambs with average weight of 18.5 kg were used. The lambs were born to ewes that did not receive supplemental selenium for the last 45 days of pregnancy or during lactation. Lambs were weaned at approximately two months of age and placed in plastic pens with plastic feeders and stainless steel waterers. For 56 days lambs were fed feedstuff low in selenium. Jugular blood samples were obtained from all lambs on days 0, 28 and 56. At the end of the 56-day depletion period, lambs were stratified by weight and randomly assigned to three treatments. The treatments consisted of: 1) Control, 2) sodium selenite, 3) L-selenomethionine and 4) zinc L-selenomethionine. The selenium sources were added to provide 0.05 ppm of supplemental selenium for 28 days and then the amount of selenium from each source was increased to 0.1 ppm for additional 28 days. Blood samples were collected via jugular puncture on days 0, 14, 28 and 56. Whole blood and plasma glutathione peroxidase activity in samples obtained on days 0, 14, 28, and 56. Plasma selenium was measured in samples obtained on days 0, 28, and 56. Six lambs from each treatment were slaughtered at the end of the study and samples of liver, kidney, muscle, and heart were obtained for the determination of selenium and glutathione peroxidase activities.

Weight gain for lambs during the depletion period averaged 196 g/day. By the 28 day of the depletion period both plasma and whole blood glutathione peroxidase activity had decreased to 75, and 57% of the initial value. These values were 48% of initial values by day 56. Lambs receiving supplemental selenium gained weight faster than those in the control group during the study. However, initial and final bodyweights were not affected by selenium source.

The addition of 0.05 ppm of selenium to the diet greatly increased plasma glutathione peroxidase activity by day 14 and activity was increased further by days 28 and 56. On day 14, glutathione peroxidase activity was not significantly affected by selenium source. However, on day 28 glutathione peroxidase activity was higher in lambs supplemented with L-selenomethionine or zinc L-selenomethionine compared with those receiving sodium selenite. There was no difference between lambs receiving L-selenomethionine and those receiving zinc L-selenomethionine. Increasing the level of supplemental selenium from 0.05 to 0.10 ppm on day 28 resulted in only small increases in plasma glutathione peroxidase activity by day 56.

Lambs supplemented with selenium in their diet had higher whole blood glutathione peroxidase activity on day 14 than controls. However, there was no difference between lambs supplemented with sodium selenite L-selenomethionine or zinc L-selenomethionine. No further increases in whole blood glutathione peroxidase activity were observed at 28 and 56 days after selenium supplementation.

Lambs supplemented with selenium for 56 days had higher glutathione peroxidase activity in heart, kidney, liver, and muscle than control lambs. Supplementation with zinc L-selenomethionine or L-selenomethionine produced higher activities in kidney, liver, and muscle compared to those produced by sodium selenite.

Plasma selenium concentrations were much higher on day 28 in animal supplemented with selenium and there was no difference between sodium selenite and L-selenomethionine or zinc L-selenomethionine. However, by day 56 lambs supplemented with L-selenomethionine or zinc L-selenomethionine had higher plasma selenium than lambs receiving sodium selenite.

Tissue selenium concentrations in all tissues were higher in lambs receiving selenium supplementation compared to control. Lambs receiving L-selenomethionine or zinc L-selenomethionine had higher heart and liver selenium concentrations than lambs receiving sodium selenite. The bioavailability of zinc L-selenomethionine and L-selenomethionine relative to sodium selenite was calculated and summarized in Table 1. It is clear from the table that zinc L-selenomethionine is more bioavailabe than sodium selenite and L-selenomethionine

TABLE 1

Relative Bioavailability of Sodium Selenite L-Selenomethionine And Zinc L-Selenomethionine Based on Increases in Glutathione Peroxidase Activity And Tissue Selenium Concentrations

| Parameter | Sodium Selenite | L-Selenomethionine | Zn L-Selenomethionine |
|---|---|---|---|
| Glutathione Peroxidase Activity | | | |
| Plasma, day 14 | 100 | 124 | 145 |
| Plasma, day 28 | 100 | 138 | 149 |
| Heart | 100 | 107 | 126 |
| Kidney | 100 | 100 | 128 |
| Liver | 100 | 161 | 152 |
| Muscle | 100 | 186 | 200 |
| Tissue Selenium Concentration | | | |
| Liver | 100 | 206 | 160 |
| Muscle | 100 | 133 | 85 |
| Heart | 100 | 139 | 158 |
| Kidney | 100 | 59 | 74 |

EXAMPLE 6

Comparison of the Effects of Sodium Selenite and Zinc L-Selenomethionine on the Performance and Tissue Selenium Concentrations in Grow-Finish Pigs:

Sixteen pigs with an average weight of 22.9 kg were stratified by weight within sex and randomly assigned to treatments consisting of 0.3 ppm supplemental selenium from either sodium selenite or zinc L-selenomethionine hydrochloride. Pigs were housed in pens and each treatment consisted of four replicate pens each housed one gilt and one sow. Pigs were fed diets that were formulated to meet NRC requirements. Pigs were fed the growing diet for 56 days and then the finishing diet for 33 days. The average pig weight at the end of the growing and finishing phases was 69.6 and 101.2 kg, respectively. Body weights of each pig were determined initially and at the end of the growing and finishing phases. At the end of the study, pigs were slaughtered and samples of liver, muscle, heart and kidney were collected for selenium determination. The results are summarized in Table 2.

Weight gain in the pigs was not affected by the selenium source during the growing or finishing phase. However, pigs receiving zinc L-selenomethionine hydrochloride consumed less feed during the finishing phase than pigs receiving sodium selenite. Therefore, the gain/feed ratio was higher for pigs fed zinc L-selenomethionine compared to pigs receiving sodium selenite. Pigs fed zinc L-selenomethionine had higher selenium concentrations in liver, muscle and heart than pigs supplemented with sodium selenite. Kidney selenium concentrations were similar in pigs whether they were fed sodium selenite or zinc L-selenomethionine.

TABLE 2

Comparison of the Effects of Sodium Selenite And Zinc L-Selenomethionine on the Performance and Tissue Selenium Concentrations in Pigs

| Parameter | Sodium Selenite | Zn L-Selenomethionine |
|---|---|---|
| Performance Growing Phase | | |
| Gain, kg/day | 0.81 | 0.86 |
| Feed Intake, kg | 1.74 | 1.86 |
| Feed/Gain | 2.15 | 2.16 |

TABLE 2-continued

Comparison of the Effects of Sodium Selenite And
Zinc L-Selenomethionine on the Performance
and Tissue Selenium Concentrations in Pigs

| Parameter | Sodium Selenite | Zn L-Selenomethionine |
|---|---|---|
| Finishing Phase | | |
| Gain, kg/day | 0.95 | 0.96 |
| Feed Intake, kg | 2.57 | 2.22 |
| Feed/Gain | 2.71 | 2.31 |
| Total | | |
| Gain, kg/day | 0.86 | 0.90 |
| Feed Intake, kg | 2.05 | 2.00 |
| Feed/Gain | 2.38 | 2.22 |
| Tissue Selenium Concentration, µg/g Dry Tissue | | |
| Liver | 1.92 | 2.97 |
| Muscle | 0.70 | 1.92 |
| Heart | 1.01 | 2.00 |
| Kidney | 9.94 | 10.40 |

EXAMPLE 7

Comparison of the Effects of Sodium Selenite and Zinc L-Selenomethionine on Plasma Selenium Concentrations and Glutathione Peroxidase Activity in Broilers:

One day old male and female birds were used in the study. Male and females were housed separately and randomly assigned to 6 blocks of 8 pens each (4 females and 4 males). The pens contained 50 females or 45 males. Two extra birds were added to each pen at the start of the experiment to allow for mortality and culls. On day 7 the number of birds in each per were adjusted to 50 females and 45 males. Three treatments were assigned to pens using a complete randomized block design. The treatments included: 1) negative control (no additional selenium), 2) sodium selenite, and 3) zinc L-selenomethionine. Birds were housed in concrete floor pens of an environmentally controlled facility. Environmental conditions were similar for all birds in all experimental groups. Water and feed were provided ad libitum throughout the study. All birds were placed on their respective treatment diets upon receipt. All feed added and removed from pens from day 0 to the end of the study was weighed and recorded. The test facility pens and birds were observed twice daily for general flock condition, lighting, water, feed, ventilation and any unanticipated changes. Noted variations were noted in writing. Birds were weighed per pen on day 0 and day 49. The feed intake for each pen was determined by subtracting the amount of feed remaining in the feeder at the end of the study period from the amount of feed weighed into the pen. Average bird weight was calculated on a pen basis. Six birds were randomly selected from each pen on day 49 for blood and muscle sample collections. Blood was collected in heparinized tubes, plasma was separated and stored at −20° C. until analyzed for selenium and glutathione peroxidase. After bleeding, the birds were killed by cervical dislocation. A 100 g sample of the right breast was collected from each bird and stored at −20° C. until analyzed for selenium. The results are summarized in TABLE 3.

TABLE 3

Increases in Plasma Selenium Concentration and
Glutathione Peroxidase Activity in Broilers

| Parameter | Control* | Sodium Selenite | Zn L-Selenomethionine |
|---|---|---|---|
| Glutathione Peroxidase Activity | 10.5 | 14.0 | 14.9 |
| Plasma Selenium Concentration, ppm | 0.114 | 0.145 | 0.177 |

What is claimed is:

1. A zinc L-seleno-alpha amino 1:1 acid complex salt compound.

2. A compound of claim 1 wherein the seleno-amino acid is L-selenomethionine 2 amino acid is methionine.

3. A compound of claim 1 wherein the seleno-amino acid is Se-methyl-L-selenocysteine.

4. A compound of claim 1 wherein the complex salt is an inorganic acid salt.

5. A compound of claim 3 wherein the inorganic acid salt is a salt derived from a halogen acid, sulfuric acid or phosphoric acid.

6. A zinc L-selenomethionine 1:1 complex salt of the formula:

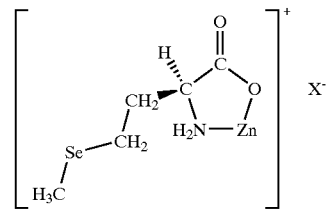

wherein X is the anion, and is selected from the group of inorganic acids of hydrochloric, sulfuric and phosphoric.

7. A method of assuring adequate dietary requirements of selenium for livestock, comprising:
adding as a feed ration supplement, a small but selenium enhancing effective amount of a zinc L-seleno-alpha amino acid 1:1 complex salt compound to the daily feed ration.

8. The method of claim 7 wherein the amount of supplement is added to swine and poultry feed to provide from 0.05 ppm to 2.0 ppm selenium.

9. The method of claim 7 wherein the amount of feed ration supplement is from 0.05 ppm to 0.5 ppm.

10. The method of claim 7 wherein the amount of supplement is added to swine and poultry feed to provide from 0.1 ppm to 0.3 ppm selenium.

11. The method of claim 7 wherein the amount of supplement is added to cattle feed to provide from 0.05 to 10 mg selenium per head per day.

12. The method of claim 7 wherein the amount of supplement is added cattle feed to provide from 2.0 to 7.0 mg selenium per head per day.

* * * * *